(12) United States Patent
Morita

(10) Patent No.: US 9,480,810 B2
(45) Date of Patent: *Nov. 1, 2016

(54) OXYGEN CONCENTRATOR

(71) Applicant: SMC CORPORATION, Chiyoda-ku (JP)

(72) Inventor: Kosuke Morita, Tsukubamirai (JP)

(73) Assignee: SMC CORPORATION, Chiyoda-ku (JP)

( * ) Notice: Subject to any disclaimer, the term of this patent is extended or adjusted under 35 U.S.C. 154(b) by 5 days.

This patent is subject to a terminal disclaimer.

(21) Appl. No.: 14/595,557

(22) Filed: Jan. 13, 2015

(65) Prior Publication Data

US 2015/0209544 A1 Jul. 30, 2015

(30) Foreign Application Priority Data

Jan. 24, 2014 (JP) ................................. 2014-011276

(51) Int. Cl.
*B01D 53/02* (2006.01)
*A61M 16/10* (2006.01)
*B01D 53/047* (2006.01)

(52) U.S. Cl.
CPC .......... *A61M 16/101* (2014.02); *B01D 53/047* (2013.01); *A61M 2202/0208* (2013.01); *B01D 2253/116* (2013.01); *B01D 2256/12* (2013.01); *B01D 2257/102* (2013.01); *B01D 2259/402* (2013.01); *B01D 2259/40083* (2013.01)

(58) Field of Classification Search
CPC .................. A61M 16/101; A61M 2202/0208; B01D 2253/116; B01D 2256/12; B01D 2257/102; B01D 2259/40083; B01D 2259/402; B01D 53/047
See application file for complete search history.

(56) References Cited

U.S. PATENT DOCUMENTS

| 4,838,257 | A | * | 6/1989 | Hatch | A61M 16/00 128/204.18 |
|---|---|---|---|---|---|
| 5,114,441 | A | * | 5/1992 | Kanner | B01D 53/0407 95/122 |
| 7,550,023 | B2 | * | 6/2009 | Schuster | B01D 45/18 210/443 |
| 2007/0169623 | A1 | * | 7/2007 | Lee | B01D 53/0415 95/101 |
| 2009/0167698 | A1 | * | 7/2009 | Altas | G06F 3/0488 345/173 |
| 2010/0192775 | A1 | * | 8/2010 | Wang | B01D 53/047 96/116 |
| 2010/0242734 | A1 | * | 9/2010 | Maeda | A61M 16/10 96/110 |
| 2014/0013954 | A1 | * | 1/2014 | Sato | A61M 16/10 96/113 |

FOREIGN PATENT DOCUMENTS

JP 2005270680 A * 10/2005
JP 2013-132359 7/2013

OTHER PUBLICATIONS

Translation of JP 2005270680 A, Oct. 2005, Ouchi.*
U.S. Appl. No. 14/611,652, filed Feb. 2, 2015, Morita.

* cited by examiner

*Primary Examiner* — Christopher P Jones
(74) *Attorney, Agent, or Firm* — Oblon, McClelland, Maier & Neustadt, L.L.P.

(57) ABSTRACT

Branch flow channels configured respectively to supply compressed air to two sieve beds respectively are provided with air supply valves each including a diaphragm valve and an electromagnetic pilot valve for driving the diaphragm valve and configured to open and close the respective branch flow channels, a pilot flow channel configured to supply pilot air to the electromagnetic pilot valves is branched from the branch flow channels, and a check valve for preventing pilot air from flowing reversely is provided in the pilot flow channel.

15 Claims, 9 Drawing Sheets

① PVa : OPEN
② PVb : OPEN

OXYGEN CONCENTRATOR

TECHNICAL FIELD

The present invention relates for example to an oxygen concentrator configured to be used in an at home oxygen therapy that a patient having a respiratory disorder performs an oxygen inhalation at home, and generate and output oxygen at a high concentration from air in the atmosphere.

BACKGROUND ART

As an oxygen concentrator of this type, as disclosed in Patent Literature 1 for example, a configuration of a PSA (Pressure Swing Adsorption) system using an absorbing material (zeolite) having properties such as selectively adsorbing nitrogen under increased pressure and discharging the adsorbed nitrogen under reduced pressure is known, and this system is also referred to as an adsorption system.

The oxygen concentrator having the adsorption system as described above is, as illustrated in FIG. 10 includes two sieve beds Ta, Tb filled with the absorbing material (zeolite) configured to adsorb nitrogen, a compressor C configured to supply compressed air to these sieve beds Ta, Tb, respective branch flow channels Fa, Fb configured to constitute part of air supply flow channel for supplying the compressed air from the compressor C to the two sieve beds Ta, Tb, respective air supply valves PVa, PVb configured to open and close the branch flow channels Fa, Fb independently, respective air exhaust flow channels Ea, Eb configured to open the respective sieve beds Ta, Tb to the atmosphere, and respective air exhaust valves EVa, EVb configured to open and close the exhaust flow channels Ea, Eb independently.

The air supply valve PVa of the branch flow channel Fa continuing to one Ta of the two sieve beds is opened and the exhaust valve EVa of the exhaust flow channel Ea is closed, and simultaneously, the air supply valve PVb of the branch flow channel Fb continuing to the other Tb is closed and the exhaust valve EVb of the exhaust flow channel Eb is opened, so that oxygen at a high concentration can be obtained by supplying the compressed air to the one sieve bed Ta. In the meantime, since the other sieve bed Tb is decompressed, and hence nitrogen adsorbed to the zeolite is separated and discharged to the atmosphere. In addition, the air supply valves PVa, PVb and the exhaust valves EVa, EVb are switched into an inverted opening-and-closing pattern, so that oxygen at a high concentration can be obtained by supplying the compressed air to the other sieve bed Tb and, in the meantime, nitrogen adsorbed to zeolite of the one sieve bed Ta is separated and discharged to the atmosphere.

In other words, by switching the opening-and-closing pattern of the respective air supply valves PVa, PVb and the exhaust valves EVa, EVb alternately, the oxygen at a high concentration can be continuously obtained through the respective sieve beds Ta, Tb.

Now, as the air supply valves PVa, PVb and the exhaust valves EVa, EVb, a configuration in which a normally open electromagnetic pilot valve 20 is assembled to a diaphragm valve 10 as illustrated in FIG. 2 is conceivable, and is configured in such a manner that when the electromagnetic pilot valve 20 is OFF, pilot air is supplied to the diaphragm valve 10 via a pilot flow channel Fp branched from the air supply flow channel and the branch flow channels Fa, Fb and the exhaust flow channels Ea, Eb are closed and, in contrast, when the electromagnetic pilot valve 20 is ON, supply of pilot air to the diaphragm valve 10 is blocked and, in contrast, the branch flow channels Fa, Fb and the exhaust flow channels Ea, Eb are opened.

In this manner, in the case where the pilot flow channel Fp configured to supply the pilot air to the electromagnetic pilot valve 20 is branched from the air supply flow channel, immediately after the opening-and-closing pattern of the respective air supply valves PVa, PVb and the exhaust valves EVa, EVb is switched and the sieve bed configured to generate oxygen is switched from the one Ta to the other Tb, the other sieve bed Tb is in a state in which the pressure is still low due to the decompression until a moment immediately before, the pressure of the compressed air supplied from the compressor C drops temporarily as illustrated in FIG. 11, and simultaneously, the pilot pressure also drops.

On the other hand, the air supply valve PVa of the one sieve bed Ta, which is on the exhaust side, is to be supplied with pilot air and closed normally. However, since the residual pressure in the sieve bed Ta is still in a high state, the diaphragm valve 10 of the air supply valve PVa is opened because the pressures applied to both surfaces of a diaphragm 13 thereof are off-balanced (see hatched portion in FIG. 11) by dropping of the pilot pressure as described above and, consequently, exhaust air containing nitrogen at a high concentration flows temporarily reversely through the air supply flow channel and flows disadvantageously into the other sieve bed Tb, which is on the side where oxygen is generated. The problem as described above occurs also immediately after switching of the sieve bed configured to generate oxygen from the other Tb to one Ta (see dot portion in FIG. 11). In FIG. 11, vertical dot lines indicate timing of turning ON and OFF alternately of a distribution of power to the electromagnetic pilot valves 20 of the respective air supply valves PVa, PVb, that is, timing of switching of the opening-and-closing pattern of the respective air supply valves PVa, PVb and the respective exhaust valves EVa, EVb.

CITATION LIST

Patent Literature

[PTL 1] Japanese Unexamined Patent Application Publication No. 2013-132359

SUMMARY OF INVENTION

Technical Problem

A technical problem of the present invention is to prevent exhaust air of a sieve bed on an air exhaust side from flowing reversely in an air supply flow channel of compressed air and flowing into a sieve bed on a side where oxygen is generated immediately after switching of the sieve bed which is in charge of supplying the compressed air in an oxygen concentrator configured to be capable of switching the sieve bed to be supplied with the compressed air between the two sieve beds alternately so as to be capable of generating oxygen at a high concentration continuously.

Solution to Problem

In order to solve the technical problem, there is provided an oxygen concentrator of the present invention including: a compressed air supply source configured to output compressed air; first and second sieve beds including an absorbing material configured to selectively adsorb nitrogen from air under increased pressure and discharge the adsorbed nitrogen under reduced pressure integrated therein and configured to generate oxygen at a high concentration by separating nitrogen from the compressed air; an air supply flow channel configured to supply the compressed air from the compressed air supply source to the respective sieve beds respectively; and an exhaust flow channel configured to discharge exhaust air in each of the sieve beds to the atmosphere respectively, the air supply flow channel including a main flow channel connected to the compressed air supply source and first and second branch flow channels branched from the main flow channel and connected to the first and second sieve beds, first and second air supply valves provided in the first and second branch flow channels and configured to communicate the compressed air supply source with the first and second sieve beds alternately; an exhaust valve provided in the exhaust flow channel and configured to communicate the first sieve bed with the atmosphere when the first air supply valve is closed, and communicate the second sieve bed with the atmosphere when the second air supply valve is closed, wherein the air supply valves each including a diaphragm valve as a main valve and an electromagnetic pilot valve configured to drive the main valve in a direction of closing the branch flow channel by pilot air, a pilot flow channel configured to supply the pilot air to the electromagnetic pilot valves is branched from a position on the upstream side of the air supply valves in the air supply flow channel, and a check valve configured to prevent the pilot air from flowing reversely is provided in the pilot flow channel.

At this time, one pilot flow channel configured to supply the pilot air to both of the electromagnetic pilot valves of the first and second air supply valves may be branched from the air supply flow channel, or alternatively, first and second pilot flow channels configured to supply the pilot air to the respective electromagnetic pilot valves of the first and second air supply valves may be branched from the air supply flow channel respectively.

Furthermore, in a preferred embodiment of the oxygen concentrator of the invention, the first and second air supply valves and the exhaust valve are mounted on a single manifold base, the manifold base includes the air supply flow channel, the pilot flow channel branched therefrom, and the exhaust flow channel formed therein, and the check valve mounted therein, the manifold base is provided with a check valve mounting hole for inserting and mounting the check valve from the outside formed therein, the pilot flow channel is formed by a primary-side flow channel hole extending from a side wall of the check valve mounting hole to the air supply flow channel and a secondary-side flow channel hole extending from an inner portion of the check valve mounting hole to the electromagnetic pilot valve, the check valve includes a hollow outer cylinder provided with a first opening configured to communicate with the secondary-side flow channel hole at an end in an axial direction, and is fitted in the check valve mounting hole with the first opening on the inner side, and a check valve main body configured to prevent pilot air from a hollow core cylinder disposed in the outer cylinder and the secondary-side flow channel hole from flowing reversely, the pilot air from the primary-side flow channel hole is introduced into the core cylinder through first and second air introducing holes opened in side walls of the outer cylinder and the core cylinder, is introduced out from the interior of the core cylinder through an air deriving hole opened in the core cylinder, and is guided to the first opening via a periphery of the check valve main body.

Accordingly, the check valve can be mounted easily in the pilot flow channel formed in the interior of the manifold base from the outside of the manifold base.

At this time, the check valve main body may be an annular lip seal having a cross sectional shape of a V-shape opening on the first opening side of the outer cylinder or, alternatively, the air deriving hole may be formed in an end surface of the core cylinder located at the position on the first opening side of the outer cylinder and may be formed so that a poppet valve as the check valve main body provided in the outer cylinder comes into and out of contact with a valve seat formed so as to surround the air deriving hole. An air filter is preferably mounted in the core cylinder so as to cover the second air introducing holes.

In a more preferable embodiment of the oxygen concentrator of the present invention, a second opening is formed at the other end, which is on a side opposite to the first opening of the outer cylinder so that the core cylinder can be fit in the outer cylinder through the second opening, and the check valve mounting hole is hermetically closed by a sealing cap configured to close the second opening of the outer cylinder.

Advantageous Effects of the Invention

In the oxygen concentrator of the present invention, the first and second air supply valves for supplying compressed air alternately to the first and second sieve beds are provided in the air supply flow channel connected to the compressed air supply source, and the pilot flow channel configured to supply the pilot air to the electromagnetic pilot valve of the air supply valve is branched from a position on the upstream side of the air supply valve in the air supply flow channel, and the check valve configured to prevent the pilot air from flowing reversely is provided in the pilot flow channel. Therefore, even though the pressure of supplied compressed air is dropped temporarily immediately after the sieve bed configured to supply the compressed air and generate oxygen at a high concentration is switched from one to the other, the pilot pressure is prevented from dropping in the same manner, so that the required pilot pressure can be maintained. Consequently, the air supply valve connected to the sieve bed on the air exhaust side (the side of being regenerated) and configured to be closed normally can be prevented from opening and thereby causing exhaust air in the sieve bed to flow reversely in the air supply flow channel and flow into the sieve bed on the side in which the oxygen at a high concentration is generated.

DESCRIPTION OF EMBODIMENTS

Hereinafter, an embodiment of an oxygen concentrator of the present invention will be described in detail with reference to the drawings.

An oxygen concentrator 1 is configured to generate and output oxygen at a high concentration from air in the atmosphere by using an absorbing material having properties such as selectively adsorbing nitrogen from air in the atmosphere under increased pressure and discharging the adsorbed nitrogen under reduced pressure, is referred to as PSA (Pressure Swing Adsorption) system, and is used in an at home oxygen therapy that a patient having a respiratory disorder performs an oxygen inhalation at home, for example.

Figure 1:
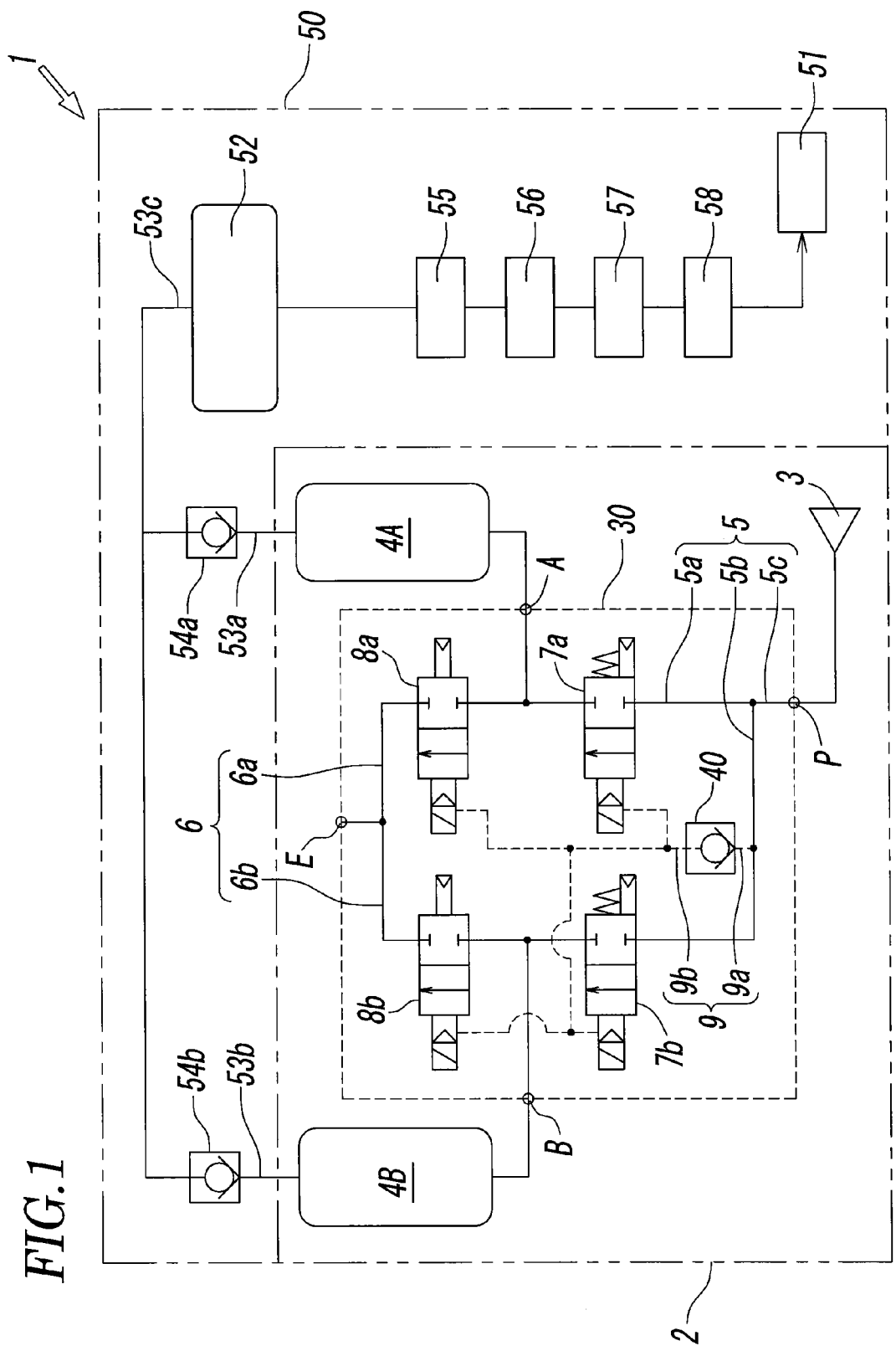
FIG. 1 is a schematic fluid circuit drawing illustrating one embodiment of an oxygen concentrator according to the present invention.

As illustrated in FIG. 1, the oxygen concentrator 1 roughly includes an oxygen generating portion 2 configured to generate oxygen at a high concentration from the atmosphere, and an oxygen supply portion 50 configured to supply the oxygen at a high concentration generated in the oxygen generating portion 2 to an output instrument 51 such as a cannula.

The oxygen generating portion 2 includes a compressor 3 as a compressed air supply source configured to compress and output air in the atmosphere, first and second sieve beds 4A, 4B having zeolite as the absorbing material integrated therein and configured to selectively separate nitrogen from the compressed air output from the compressor 3 and generate oxygen at a high concentration, an air supply flow channel 5 disposed between the compressor 3 and the respective sieve beds 4A, 4B and configured to supply the compressed air respectively to the sieve beds 4A, 4B, and an exhaust flow channel 6 configured to discharge exhaust air from the respective sieve beds 4A, 4B to the atmosphere respectively.

The air supply flow channel 5 includes a main flow channel 5c connected to the compressor 3 at one end thereof and first and second branch flow channels 5a, 5b branched at the other end of the main flow channel 5c and connected to the first and second sieve beds 4A, 4B. At a midsection of the first and second branch flow channels 5a, 5b, first and second air supply valves 7a, 7b configured to communicate the compressor 3 with the first and second sieve beds 4A, 4B alternately by opening and closing the branch flow channels 5a, 5b alternately are provided, respectively.

The exhaust flow channel 6 is formed by first and second exhaust flow channels 6a, 6b in which exhaust air from the first and second sieve beds 4A, 4B passes respectively. A first exhaust valve 8a configured to open when the first air supply valve 7a is closed to communicate the first sieve bed 4A with the atmosphere and discharge exhaust air in the first sieve bed 4A to the atmosphere is provided in the first exhaust flow channel 6a, and a second exhaust valve 8b configured to open when the second air supply valve 7b is closed to communicate the second sieve bed 4B with the atmosphere and discharge exhaust air in the sieve bed 4B to the atmosphere is provided in the second exhaust valve 6b.

Here, a single pilot flow channel 9 configured to supply pilot air to respective electromagnetic pilot valves 20 of the first and second air supply valves 7a, 7b and the first and second exhaust valves 8a, 8b described later in detail is branched from a position on the upstream side of the second air supply valve 7b in the second branch flow channel 5b.

Figure 2:
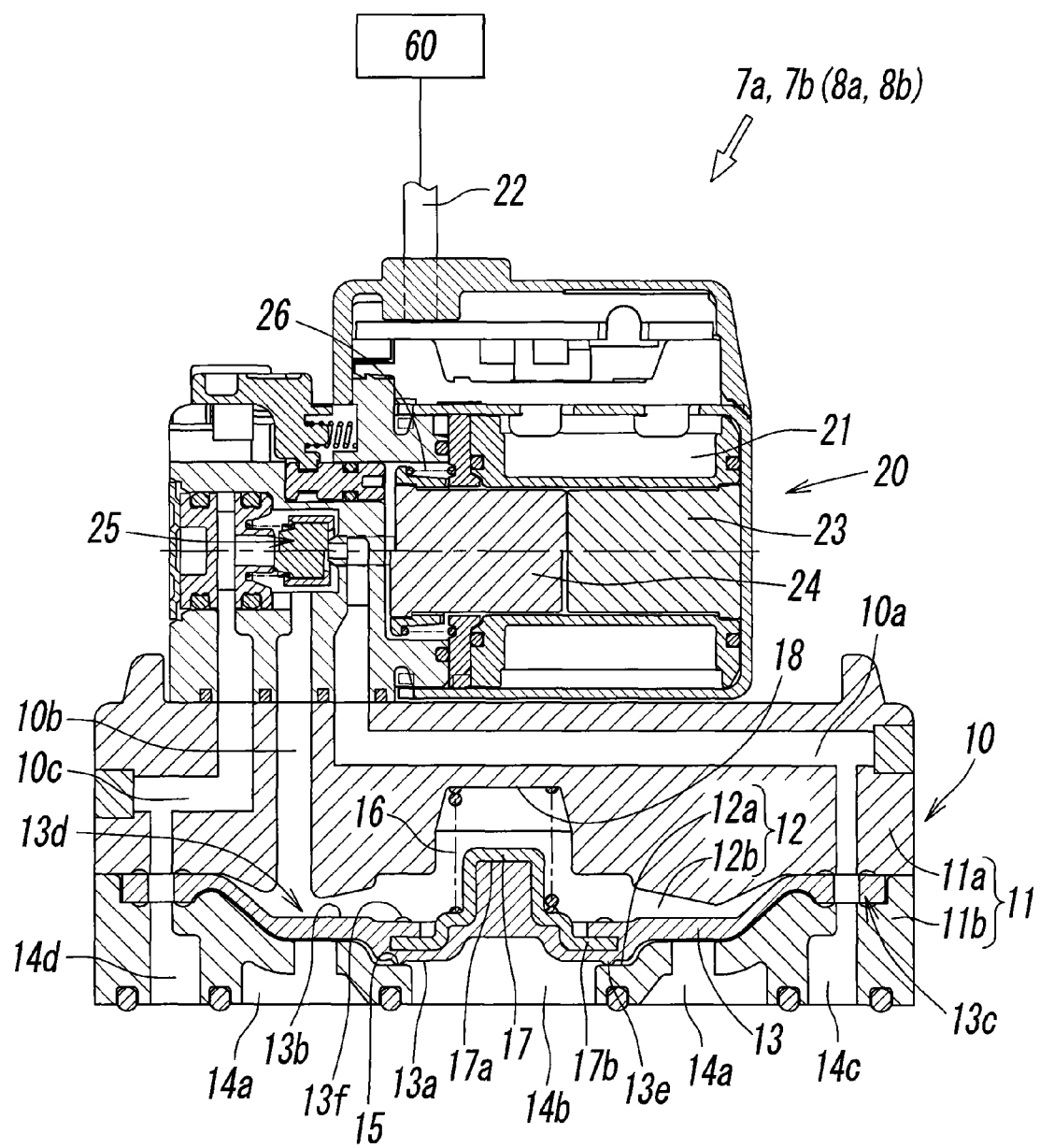
FIG. 2 is a cross-sectional view illustrating structure of an air supply valve and an exhaust valve in FIG. 1.

The respective electromagnetic pilot valves 20 are respectively connected to a control unit 60 as illustrated in FIG. 2, so that the respective valves 7a, 7b, 8a, 8b can be operated to open and close by the control unit 60.

In other words, in the oxygen concentrator 1, a "first valve opening-and-closing pattern" in which the first air supply valve 7a and the second exhaust valve 8b are opened and the second air supply valve 7b and the first exhaust valve 8a are closed to supply compressed air to the first sieve bed 4A to generate oxygen at a high concentration and, at the same time, exhaust air containing nitrogen at a high concentration in the second sieve bed 4B is discharged to the atmosphere to re-generate the sieve bed 4B, and a "second valve opening-and-closing pattern" in which the second air supply valve 7b and the first exhaust valve 8a are opened and the first air supply valve 7a and the second exhaust valve 8b are closed to supply compressed air to the second sieve bed 4B to generate oxygen at a high concentration and exhaust air containing nitrogen at a high concentration in the first sieve bed 4A is discharged to the atmosphere to re-generate the sieve bed 4A are switched alternately by the control unit 60, so that the oxygen at a high concentration can be generated continuously.

In contrast, the oxygen supply portion 50 is configured to store the oxygen at a high concentration generated in the respective sieve beds 4A, 4B of the oxygen generating portion 2 once in a tank 52, and output the oxygen at a high concentration to the output instrument 51, and includes first and second output flow channels 53a, 53b configured to output the oxygen at a high concentration from the first and second sieve beds 4A, 4B respectively and a third output flow channel 53c connected to the output instrument 51 via the tank 52 after having joined the first and second output flow channels 53a, 53b. Here, the first and second output flow channels 53a, 53b are provided with output-side check valves 54a, 54b for preventing the oxygen at a high concentration from flowing reversely from the tank 52 to the respective sieve beds 4A, 4B.

Then, the oxygen at a high concentration stored in the tank 52 is introduced to the output instrument 51 via a decompression valve 55, a flow rate regulation valve 56, a filter 57, and a moisturizer 58 provided in the third output flow channel 53c. Here, since the zeolite filled in the sieve beds 4A, 4B has a property to adsorb not only nitrogen in the air but also water content and hence the oxygen at a high concentration is output from the sieve beds 4A, 4B in an extremely dry state, the moisturizer 58 has a role to moisturize the oxygen at a high concentration.

In order to improve re-generation efficiency of the pair of sieve beds 4A, 4B and generation efficiency of the oxygen at a high concentration, the first output flow channel 53a and the second output flow channel 53b may be connected with a conduit provided with an orifice or a conduit provided with a pressure equalizing valve on the upstream side of the output-side check valves 54a, 54b.

Subsequently, configurations of the air supply valves 7a, 7b and the exhaust valves 8a, 8b will be described further in detail. The first and second air supply valves 7a, 7b each include a diaphragm valve 10 as a main valve configured to open and close the branch flow channels 5a, 5b of the air supply flow channel 5, and the electromagnetic pilot valve 20 configured to drive the diaphragm valve 10 in the direction of closing the branch flow channels 5a, 5b by pilot air introduced through the pilot flow channel 9 as illustrated in FIG. 1 and FIG. 2.

The diaphragm valve 10 includes a casing 11 including a first portion 11a and a second portion 11b divided into upper and lower portions and configured to form a space 12 in the interior thereof, and a diaphragm 13 formed of an elastic material such as rubber into a disc shape, held between the first portion 11a and the second portion 11b of the casing 11 at a peripheral edge portion 13c thereof and disposed in the space 12 at a body portion 13d on the inner side thereof. The space 12 is hermetically divided into a first drive chamber 12a formed on a first pressure receiving surface 13a side (lower surface side in the drawing) of the diaphragm 13, which is one of the surfaces, and a second drive chamber 12b formed on a second pressure receiving surface 13b side (upper surface side in the drawing) thereof, which is the other surface, by the diaphragm 13.

The casing 11 is provided with first port 14a to which the branch flow channels 5a, 5b on the compressor 3 side are connected, a second port 14b to which the branch flow channels 5a, 5b on the sieve beds 4A, 4B side are connected, a third port 14c to which the pilot flow channel 9 is connected, and a forth port 14d opening to the atmosphere for discharging exhaust air of the electromagnetic pilot valves 20 on a bottom surface thereof. The first and second ports 14a, 14b communicate with the first drive chamber 12a, and a valve seat 15 is formed on an inner surface of the space 12 in the periphery of the second port 14b so as to surround the second port 14b.

The diaphragm 13 is provided with a sealing rib 13e configured to come into and out of contact with the valve seat 15 to isolate or communicate the connecting between the first port 14a and the second port 14b formed into an annular shape on the first pressure receiving surface 13a. The body portion 13d of the diaphragm 13 moves in the space 12 toward the second drive chamber 12b only when a pressure acting on the first pressure receiving surface 13a of the diaphragm 13 becomes larger than a pressure acting on the second pressure receiving surface 13b by a predetermined amount ΔP and, consequently, the sealing rib 13e moves away from the valve seat 15 so that the first port 14a and the second port 14b communicate with each other.

In each of the air supply valves 7a, 7b of this embodiment, a metallic first spring seat 17 having a hollow projecting portion 17a and a flange portion 17b formed in the periphery thereof and having a diameter slightly larger than that of the sealing rib 13e is mounted at a center portion of the second pressure receiving surface 13b of the diaphragm 13 so that the flange portion 17b is embedded into the diaphragm 13. The interior of the projecting portion 17a of the spring seat 17 is filled with an elastic material which forms the diaphragm 13. In contrast, a second spring seat 18 having a depressed shape is formed so as to oppose the first spring seat 17 on an inner surface opposing the second pressure receiving surface 13b of the second drive chamber 12b, and a coil spring 16 as a biasing member configured to bias the body portion 13d of the diaphragm 13 toward the first drive chamber 12a is provided between the first and second spring seats.

Accordingly, the value of ΔP required for opening the diaphragm valve 10 is set to be larger value. A plurality of projections 13f arrayed in an annular shape having substantially the same diameter as the diameter of the sealing rib 13e are formed in the periphery of the first spring seat 17 on the second pressure receiving surface 13b of the diaphragm 13 so as to come into abutment with the inner surface of the second drive chamber 12b opposing the second pressure receiving surface 13b when the diaphragm valve 10 is in a fully open state to prevent the second pressure receiving surface 13b from coming into tight contact with the inner surface.

The electromagnetic pilot valve 20 includes a cylindrical solenoid 21, a power supply terminal 22 connected to the control unit 60 and configured to distribute power to the solenoid 21, a fixed iron core 23 disposed in the solenoid 21, a movable iron core 24 disposed in the solenoid 21 coaxially with the fixed iron core 23, and a valve portion 25 operated by the movement of the movable iron core 24 in the axial direction. A pilot supply channel 10a configured to introduce the pilot air from the third port 14c to which the pilot flow channel 9 is connected to the valve portion 25 of the pilot valve 20, a pilot supply-and-exhaust channel 10b configured to connect the valve portion 25 to the second drive chamber 12b of the diaphragm valve 10 and supply and discharge the pilot air to the second drive chamber 12b, and a pilot exhaust channel 10c configured to communicate the valve portion 25 to the atmosphere and exhaust the pilot air introduced out from the second drive chamber 12b to the valve portion 25 through the pilot supply-and-exhaust channel 10b to the atmosphere through the forth port 14d are formed in the interior of the casing 11 of the diaphragm valve 10.

When the power is not distributed to the solenoid 21 (at the time of OFF), the movable iron core 24 is separated from the fixed iron core 23 by a biasing force of a spring 26, the pilot supply channel 10a and the pilot supply-and-exhaust channel 10b are brought into communication with each other by the valve portion 25, so that the pilot air is introduced from the pilot flow channel 9 to the second drive chamber 12b of the diaphragm valve 10. Accordingly, the body portion 13d of the diaphragm 13 moves toward the first drive chamber 12a against the pressure acting on the first pressure receiving surface 13a, and the sealing rib 13e is pressed against the valve seat 15 so that the branch flow channels 5a, 5b are closed.

In contrast, when the power is distributed to the solenoid 21 (at the time of ON), the movable iron core 24 is adsorbed by the fixed iron core 23, the pilot supply-and-exhaust channel 10b and the pilot exhaust channel 10c are brought into communication with each other by the valve portion 25, so that the pilot air is discharged from the second drive chamber 12b to the atmosphere. Accordingly, the body portion 13d of the diaphragm 13 moves toward the second drive chamber 12b against a biasing force of the coil spring 16 acting on the second pressure receiving surface 13b, so that the sealing rib 13e moves away from the valve seat 15 so that the branch flow channels 5a, 5b are opened.

In other words, the electromagnetic pilot valve 20 is a normally open solenoid valve, and is configured in such a manner that the branch flow channels 5a, 5b are closed by the diaphragm valve 10 to block the supply of the compressed air to the sieve beds 4A, 4B at the time when the power is not distributed (at the time of OFF), and the branch flow channels 5a, 5b are opened by the diaphragm valve 10 to allow the compressed air to be supplied to the sieve beds 4A, 4B at the time when the power is distributed (at the time of ON).

The exhaust valves 8a, 8b may basically have the same structure as the air supply valves 7a, 7b illustrated in FIG. 2. However, in this embodiment, the coil spring 16 is omitted as illustrated in FIG. 1 as well.

When the power is not distributed to the electromagnetic pilot valve 20, the exhaust flow channels 6a, 6b are closed by the diaphragm valve 10, and hence the sieve beds 4A, 4B are isolated from the atmosphere, and when the power is distributed, the exhaust flow channels 6a, 6b are opened by the diaphragm valve 10 so that exhaust air from the sieve beds 4A, 4B is discharged to the atmosphere.

Figure 11:
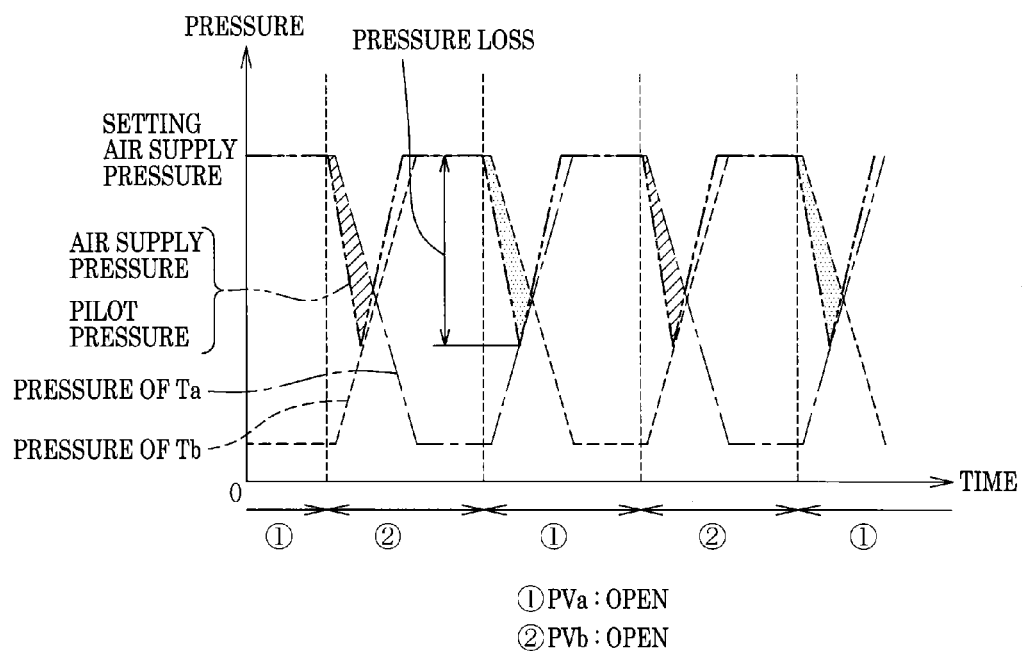
FIG. 11 is a schematic graph illustrating pressure variations in the fluid circuit in FIG. 10.

In the case where the air supply valves 7a, 7b of the diaphragm type as described above are used, when the sieve bed in charge of generating oxygen is switched from the first sieve bed 4A to the second sieve bed 4B, for example, that is, when the pattern is switched from the "first valve opening-and-closing pattern" to the "second valve opening-and-closing pattern", the second sieve bed 4B is in a state in which internal pressure is still lower at the moment immediately after by the exhaust air until immediately before. Therefore, the pressure of the compressed air to be supplied from the compressor 3 through the air supply flow channel 5 drops temporarily as illustrated in FIG. 11. In contrast, at that time, internal pressure of the first sieve bed 4A is still in a high state by the air supply until immediate before.

If the pilot pressure supplied to the electromagnetic pilot valve 20 drops simultaneously through the pilot flow channel 9 branched from the air supply flow channel 5, a high internal pressure of the first sieve bed 4A is applied to the first drive chamber 12a of the diaphragm valve 10 of the first air supply valve 7a through the second port 14b, and the dropped pilot pressure is applied to the second drive chamber 12b through the third port 14c.

Then, although the diaphragm valve 10 of the first air supply valve 7a is normally to be closed by a supply of the pilot air, the diaphragm valve 10 is opened by an amount more than the value of ΔP required for opening the diaphragm valve 10 (see hatched portion in FIG. 11) from the reasons described above and, consequently, exhaust air from the first sieve bed 4A containing nitrogen at a high concentration flows temporarily reversely in the air supply flow channel 5 and flows into the second sieve bed 4B, which is a side where oxygen is generated.

Such a problem also occurs when the sieve bed in charge of generating oxygen is switched from the second sieve bed 4B to the first sieve bed 4A, that is, immediately after switching from the "second valve opening-and-closing pattern" to the "first valve opening-and-closing pattern" (See dot portion in FIG. 11).

Figure 3:
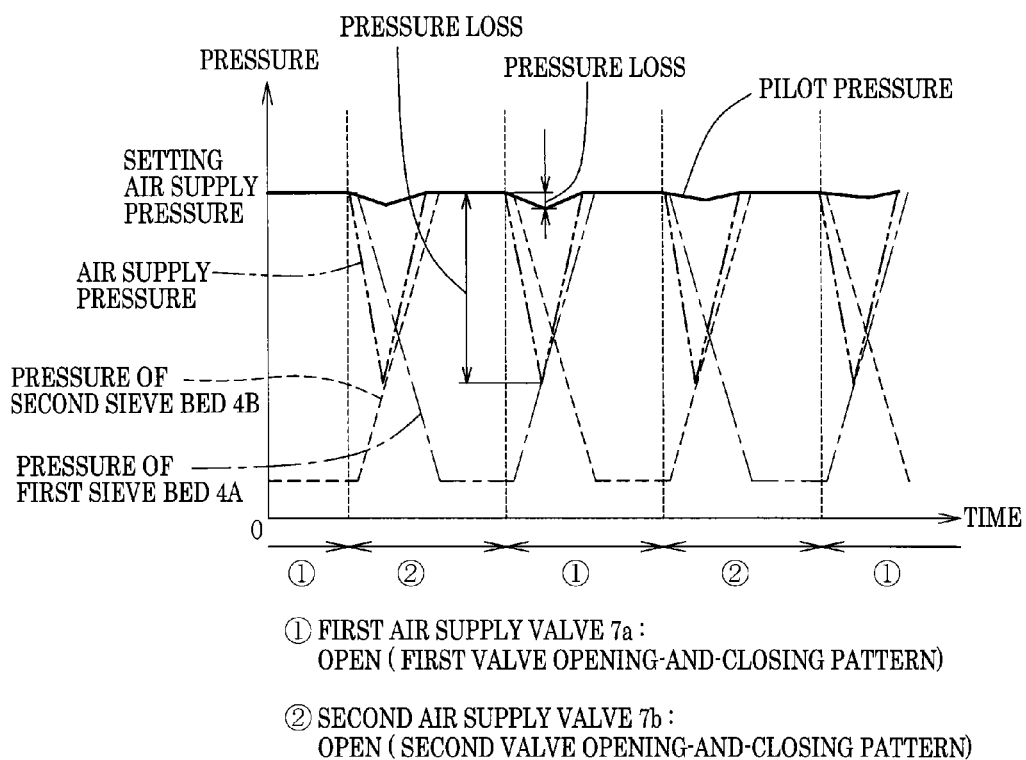
FIG. 3 is a schematic graph illustrating pressure variations in the fluid circuit in FIG. 1.
Figure 4A:
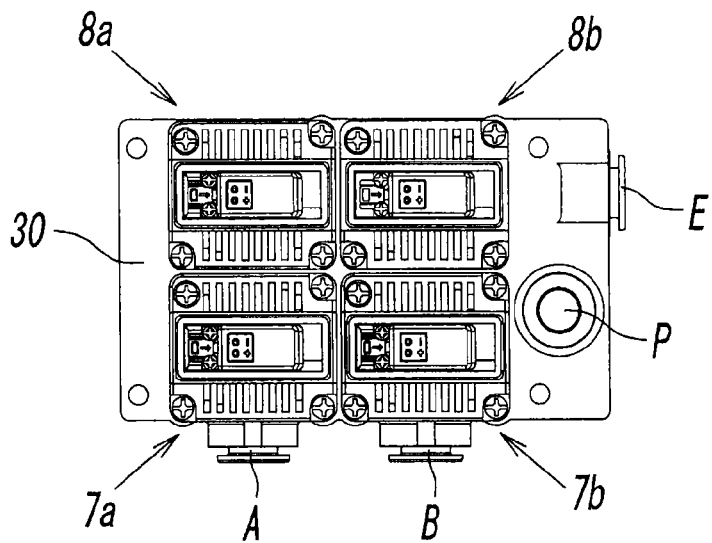
FIG. 4A is a plan view illustrating a state in which the respective air supply valves and the respective exhaust valves are mounted on a manifold base.
Figure 4B:
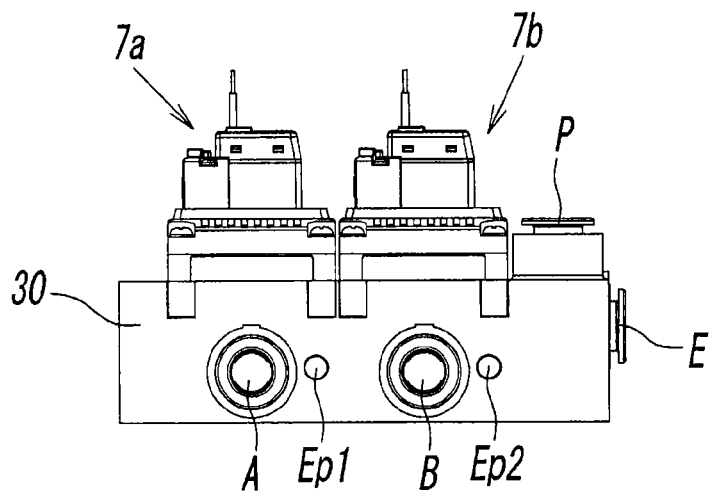
FIG. 4B is a front view illustrating a state in which the respective air supply valves and the respective exhaust valves are mounted on a manifold base.
Figure 4C:
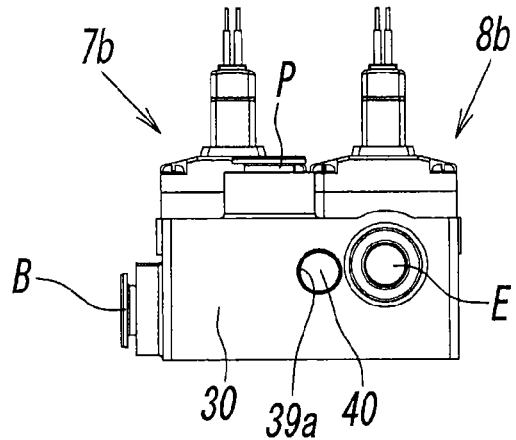
FIG. 4C is a side view illustrating a state in which the respective air supply valves and the respective exhaust valves are mounted on a manifold base.

Therefore, in this embodiment, as illustrated in FIG. 1, a pilot check valve 40 for maintaining the pilot pressure by preventing the pilot air from flowing reversely from the electromagnetic pilot valve 20 side toward the air supply flow channel 5 is provided at a position of the upstream side of the electromagnetic pilot valves 20 of the respective air supply valves 7a, 7b in the pilot flow channel 9 (that is, the air supply flow channel 5 side). Accordingly, as illustrated in FIG. 3, even though the air supply pressure drops, the pilot pressure is restrained from dropping correspondingly, and hence the required pilot pressure can be maintained. Consequently, the air supply valve connected to the sieve bed on the air exhaust side (the side of being regenerated) and configured to be closed normally can be prevented from opening and thereby causing exhaust air in the sieve bed to flow reversely in the air supply flow channel 5 and flow into the sieve bed on the side in which the oxygen at a high concentration is generated. In FIG. 3, vertical dot lines indicate timing of turning ON and OFF of a distribution of power to the electromagnetic pilot valves 20 of the respective air supply valves 7a, 7b by the control unit 60, that is, timing of switching of the first valve opening-and-closing pattern and the second valve opening-and-closing pattern alternately by the control unit 60.

The configuration of an air pressure circuit including the pilot check valve 40 in the oxygen generating portion 2 will be described further in detail. The air pressure circuit of the oxygen generating portion 2 is formed by a valve assembly formed by the first and second air supply valves 7a, 7b and the first and second exhaust valves 8a, 8b mounted on a single manifold base 30 as illustrated in FIG. 1, FIG. 4A to FIG. 5. In other words, the manifold base 30 is integrally molded in a substantially rectangular parallelepiped, and is mounted in a state in which the respective air supply valves 7a, 7b and the respective exhaust valves 8a, 8b are adjacent to each other in a two by two pattern on the plane thereof.

The manifold base 30 includes an air supply port P to which the main flow channel 5c of the air supply flow channel 5 on the compressor 3 side is connected on the plane, and the main flow channel 5c is branched in the interior thereof into the first branch flow channel 5a and the second blanch flow channel 5b. A front surface of the manifold base 30 is provided with a first output port A and a second output port B to which the first and second sieve beds 4A, 4B are connected, and a side surface of the manifold base 30 is provided with an air exhaust port E for discharging exhaust air from the respective exhaust flow channels 6a, 6b formed in the interior thereof to the atmosphere. In the interior of the manifold base 30, the pilot flow channel 9 is branched from the second branch flow channel 5b.

Figure 5:
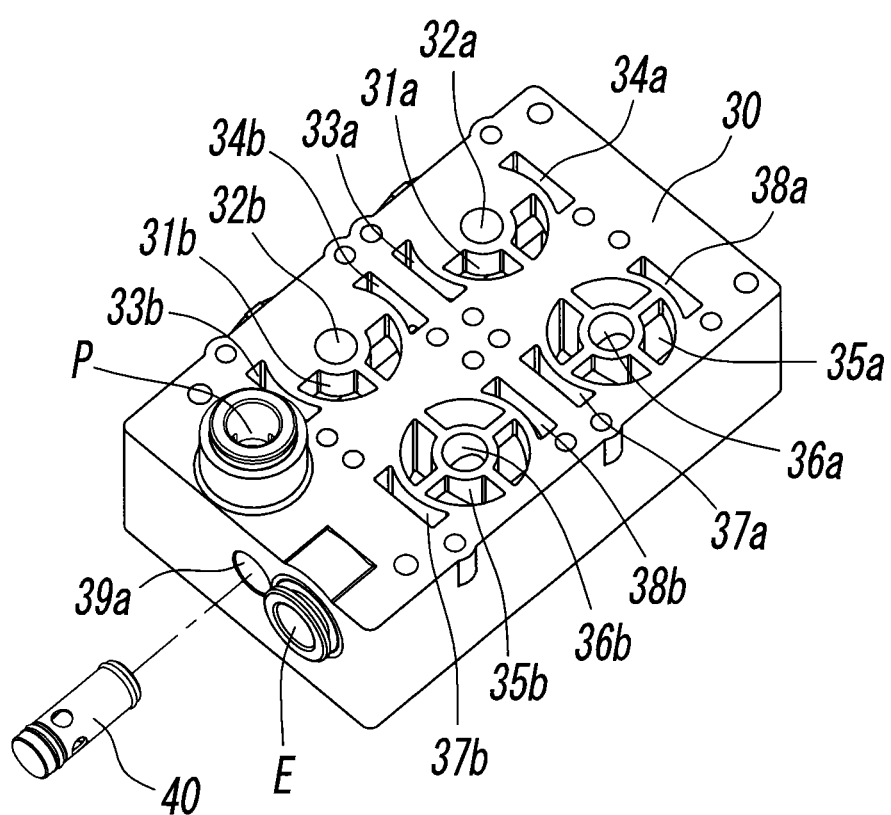
FIG. 5 is a perspective view illustrating an appearance of the manifold base, an appearance and a method of mounting a pilot check valve.

As illustrated in FIG. 5, first air supply side openings 31a, 31b in communication with the air supply port P and connected respectively to the first ports 14a of the first and second air supply valves 7a, 7b, second air supply side openings 32a, 32b in communication respectively with the first and second output ports A, B, and connected respectively to the second ports 14b of these valves, third air supply side openings 33a, 33b in communication with the pilot flow channel 9, and connected respectively to the third ports 14c of these valves, and fourth air supply side openings 34a, 34b in communication respectively with first and second pilot exhaust port Ep1, Ep2 formed adjacent to the output ports A, B respectively, and connected respectively to the fourth ports 14d of these valves are disposed respectively in a concentric pattern on a plane of the manifold base 30.

In addition, first air exhaust side openings 35a, 35b in communication respectively with the first and second output ports A, B, and connected respectively to the first ports 14a of the first and second exhaust valves 8a, 8b, second air exhaust side openings 36a, 36b in communication with the air exhaust port E, and connected respectively to the second ports 14b of these valves, third air exhaust side openings 37a, 37b in communication with the pilot flow channel 9, and connected respectively to the third ports 14c of these valves, and fourth air exhaust side openings 38a, 38b in communication respectively with the first and second pilot exhaust port Ep1, Ep2, and connected respectively to the fourth ports 14d of these valves are disposed respectively in a concentric pattern on the same plane.

Figure 6:
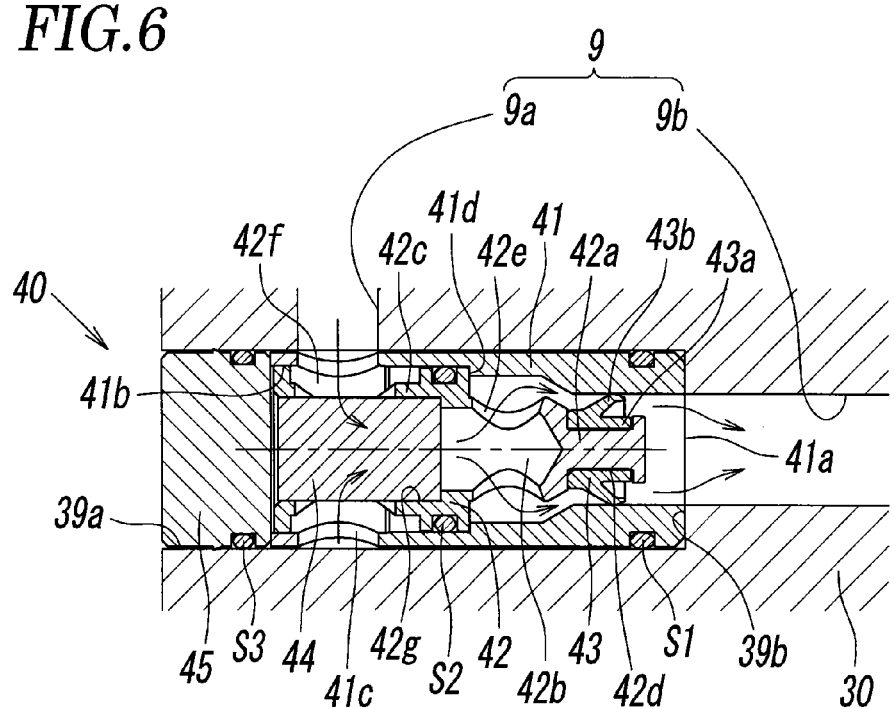
FIG. 6 is an enlarged cross-sectional view of a principal portion of a state in which the pilot check valve is mounted on the manifold base.

The manifold base 30 is provided with a check valve mounting hole 39a for inserting the pilot check valve 40 from the outside into the interior thereof for being mounting in the pilot flow channel 9 so as to be opened adjacent to the air exhaust port E. As illustrated in FIG. 6, in the manifold base 30, the pilot flow channel 9 is formed by a primary-side flow channel hole 9a on the upstream side and a secondary-side flow channel hole 9b on the downstream side with the check valve 40 interposed therebetween. The primary-side flow channel hole 9a is provided on a side wall biased to the opening of the check valve mounting hole 39a and communicates with the second branch flow channel 5b, and the secondary-side flow channel hole 9b is opened on a bottom portion of the check valve mounting hole 39a in the inner side and communicates with the electromagnetic pilot valves 20 of the respective valves 7a, 7b, 8a, 8b via the third air supply side openings 33a, 33b and the third air exhaust side openings 37a, 37b. The primary-side flow channel hole 9a and the secondary-side flow channel hole 9b are formed to have a diameter smaller than the check valve mounting hole 39a, and a shouldered portion 39b at a boundary between the check valve mounting hole 39a and the secondary-side flow channel hole 9b serves as a positioning and stopper of the pilot check valve 40 described below in detail.

Figure 7:
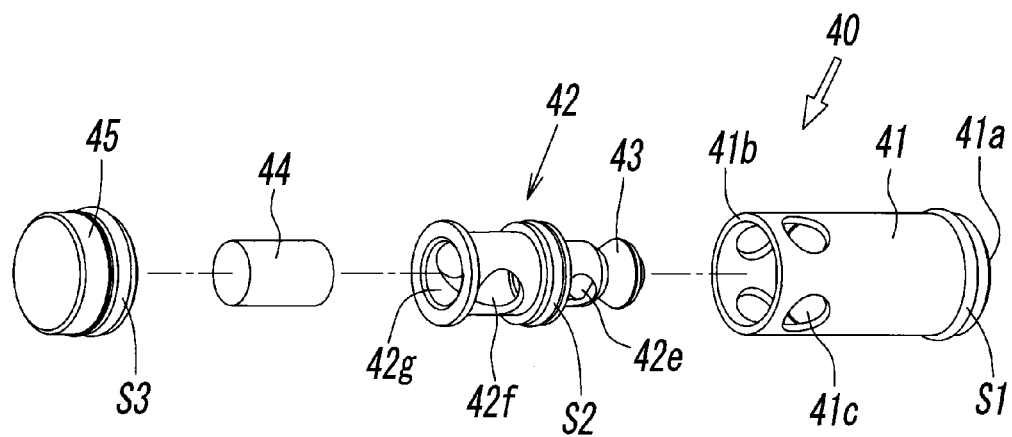
FIG. 7 is an exploded perspective view of the pilot check valve.

The pilot check valve 40 is configured to prevent the pilot air from flowing from the secondary-side flow channel hole 9b to the primary-side flow channel hole 9a reversely to maintain the pilot pressure on the downstream side as illustrated in FIG. 6 and FIG. 7, and includes a hollow outer cylinder 41 which is to be fitted into the check valve mounting hole 39a and corresponds to an exterior of the check valve 40, a hollow core cylinder 42 which is fitted into the outer cylinder 41 and forms a flow channel of the pilot air, a check valve main body 43 arranged in the interior of the same outer cylinder 41, an air filter 44 arranged in the interior of the core cylinder 42, and a sealing cap 45 configured to hermetically close the check valve mounting hole 39a.

The outer cylinder 41 is provided with a first opening 41a at a first end in the axial direction thereof, and a second opening 41b at a second end on the opposite side, and is fitted into the check valve mounting hole 39a with the first opening 41a positioned on the inner side therein. At that time, the second opening 41b is closed by the sealing cap 45 in a state in which the first end is in abutment with the shouldered portion 39b, and the first opening 41a is in communication with the secondary-side flow channel hole 9b. A plurality of first air introducing holes 41c for introducing the pilot air into the check valve 40 are provided in the circumferential direction on a side wall of the outer cylinder 41 at a position corresponding to the primary-side flow channel hole 9a in the axial direction. In addition, an annular seal member S1 configured to hermetically seal with respect to the side wall of the check valve mounting hole 39a is mounted on an outer periphery biased to the first end with respect to the first air introducing holes 41c. The outer cylinder 41 is provided with a shouldered portion 41d on an inner surface thereof in the axial direction at a substantially center thereof, and is formed so as to be decreased in inner diameter from the second end side to the first end side. The shouldered portion 41d serves as positioning and a stopper of the core cylinder 42 described below in detail.

The core cylinder 42 includes a shaft-shaped valve mounting portion 42a having the check valve main body 43 mounted on the outer periphery thereof, a flow channel forming portion 42b forming a flow channel of the pilot air, and a cylindrical portion 42c for mounting the air filter 44 in the interior thereof arranged in this order from the first end side to the second end side on the opposite side thereof in the axial direction and integrally molded, and is fitted into the outer cylinder 41 from the second opening 41b thereof with the valve mounting portion 42a on the first end side positioned on the inner side. A groove 42d is formed on the outer periphery of the valve mounting portion 42a, and the check valve main body 43 is mounted in the groove 42d.

The flow channel forming portion 42b has a diameter larger than the valve mounting portion 42a, and is formed into a hollow cylindrical shape opening on the second end side, and includes a plurality of air deriving holes 42e arranged in the circumferential direction and configured to derive the pilot air flowing into the interior thereof from the second end side to a portion between the outer periphery of the core cylinder 42 and the inner periphery of the outer cylinder 41.

The cylindrical portion 42c has a diameter larger than that of the flow channel forming portion 42b, is formed into a hollow cylinder opening at both ends in the axial direction, and has an outer diameter substantially the same as an inner diameter of the outer cylinder 41. The first end side thereof communicates with the flow channel forming portion 42b, and a plurality of second air introducing holes 42f for introducing the pilot air into the core cylinder 42 are provided on a side wall in the circumferential direction at positions corresponding to the first air introducing holes 41c. The cylindrical portion 42c is in abutment with the shouldered portion 41d of the outer cylinder 41 at the end on the first end side thereof and is closed at the second end thereof by the sealing cap 45 in the state of being mounted in the outer cylinder 41. In addition, a seal member S2 configured to hermetically seal against the inner wall of the outer cylinder 41 is mounted on an outer periphery of the cylindrical portion 42c at a position biased to the first end with respect to the second air introducing holes 42f.

In addition, the check valve main body 43 includes an annular base portion 43a extending in parallel to the axis and fitted into the groove 42d of the valve mounting portion 42a as illustrated in FIG. 6, and an annular lip portion 43b provided so as to be inclined from the outer periphery of the base portion 43a toward the first opening 41a of the outer cylinder 41, and is integrally molded of elastic material such as rubber. In other words, the check valve main body 43 is formed of a lip seal having an annular shape and formed into a substantially V-shape opening toward the first opening 41a in cross section, and a distal end of the lip portion 43b is in abutment with the inner surface of the outer cylinder 41 in a state in which the core cylinder 42 is mounted in the interior of the outer cylinder 41. Accordingly, with respect to the flow of the pilot air from the primary-side flow channel hole 9a side, the lip portion 43b falls over to form a flow channel with respect to the inner surface of the outer cylinder 41, thereby allowing the flow toward the secondary-side flow channel hole 9b, and with respect to the flow from the secondary-side flow channel hole 9b side, the lip portion 43b rises up and hence the distal end thereof is pressed against the inner surface of the outer cylinder 41 thereby blocking the flow channel, and hence the flow toward the primary-side flow channel hole 9a is prevented.

The air filter 44 is formed into a cylindrical shape having substantially the same diameter and the axial length as the shape of a flow channel chamber 42g in the cylindrical portion 42c so as to be mountable by being inserted into the flow channel chamber 42g from the second end side of the cylindrical portion 42c. The air filter 44 covers the entire part of the second air introducing holes 42f in the state of being mounted in the flow channel chamber 42g.

The sealing cap 45 is formed into a solid disc shape in the axial direction, and a seal member S3 configured to hermetically seal with respect to the inner surface of the outer cylinder 41 is mounted on the outer periphery thereof. At this time, the sealing cap 45 may be configured to be demountably mountable with respect to the check valve mounting hole 39a, so that the maintenance of the check valve 40 can be performed as needed.

In the pilot flow channel 9 provided with the pilot check valve 40 as described above, the pilot air from the primary-side flow channel hole 9a is introduced into the cylindrical portion 42c through the first and second air introducing holes 41c, 42f opening respectively on the side wall of the outer cylinder 41 and the side wall of the cylindrical portion 42c of the core cylinder 42. Then, the pilot air is filtered by the air filter 44 mounted in the cylindrical portion 42c, then flows into the flow channel forming portion 42b of the core cylinder 42, is derived out to a portion between the outer surface of the core cylinder 42 and the inner surface of the outer cylinder 41 through the air deriving holes 42e, and is guided to the first opening 41a of the outer cylinder 41 communicating with the secondary-side flow channel hole 9b through the periphery of the check valve main body 43. In contrast, the flow from the secondary-side flow channel hole 9b toward the primary-side flow channel hole 9a is prevented by the check valve main body 43.

Therefore, even though air supply pressure in the air supply flow channel 5 drops, the pilot pressure of the pilot flow channel 9 can be maintained. In addition, the pilot check valve 40 can be mounted easily in the pilot flow channel 9 formed in the interior of the manifold base 30 from the outside of the manifold base 30.

Figure 8:
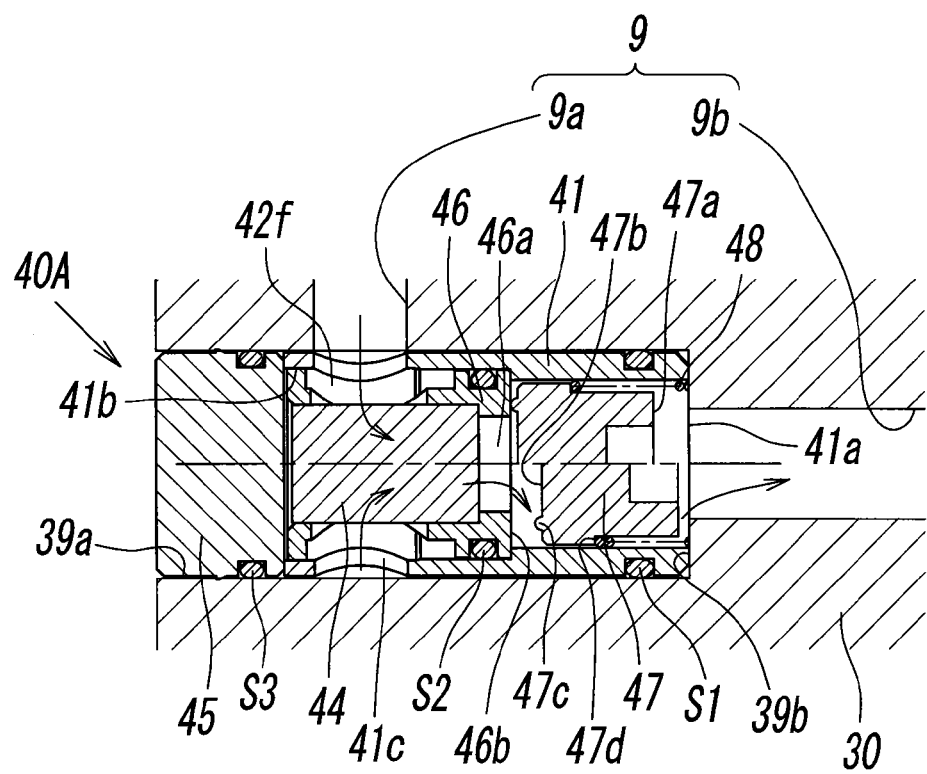
FIG. 8 is an enlarged cross-sectional view of a principal portion of a modification of the pilot check valve.

FIG. 8 illustrates a modification 40A of the pilot check valve. Here, in order to avoid overlapping of description, portions having different configurations from the pilot check valve 40 illustrated in FIG. 6 are mainly described, and description of the parts having the same configurations is omitted by denoting with the same reference numerals as those illustrated in FIG. 6.

In the pilot check valve 40A of this modification, a core cylinder 46 has a configuration in which the valve mounting portion 42a and the flow channel forming portion 42b are omitted from the core cylinder 42 of the check valve 40, that is, has the same form as the cylindrical portion 42c. The core cylinder 46 includes an air deriving hole 46a configured to derive the pilot air from the interior of the core cylinder 46 into the outer cylinder 41, and a valve seat 46b formed in the periphery of the air deriving hole 46a so as to surround the air deriving hole 46a on an end surface of the outer cylinder 41 located on the first opening 41a side.

A check valve main body 47 formed of a poppet valve is provided in the outer cylinder 41 adjacent to the core cylinder 46 in the axial direction. The check valve main body 47 is disposed coaxially on the first opening 41a side of the core cylinder 46, and is inserted into the outer cylinder 41 so as to be capable of moving reciprocally along the axis, and the first end on the first opening side and the second end on a side opposite thereto (the core cylinder 46 side) in the axial direction form first and second pressure receiving surfaces 47a, 47b, respectively. An annular sealing rib 47c configured to be brought into and out of contact with the valve seat 46b in association with the reciprocal motion of the check valve main body 47 is provided at a position on the second pressure receiving surface 47b on the core cylinder 46 side so as to project therefrom. The check valve main body 47 includes a spring seat 47d on the outer periphery thereof, is biased toward the core cylinder 46 by a coil spring 48 as a biasing member provided between the spring seat 47d and the shouldered portion 39b of the check valve mounting hole 39a, so that the sealing rib 47c is brought into abutment with the valve seat 46b by a biasing force thereof.

In this configuration, with respect to the flow of the pilot air from the primary-side flow channel hole 9a side, the check valve main body 47 is slid by the pressure applied to the second pressure receiving surface 47b of the check valve main body 47 toward the first opening side along the axial direction and the sealing rib 47c moves away from the valve seat 46b, so that the pilot air is allowed to flow from the air deriving hole 46a of the core cylinder 46 toward the first opening through a gap between an outer peripheral surface of the check valve main body 47 and an inner peripheral surface of the outer cylinder 41. In contrast, with respect to the flow from the secondary-side flow channel hole 9b side, the check valve main body 47 is slid by the pressure applied to the first pressure receiving surface 47a toward the core cylinder 46 side along the axial direction, and the sealing rib 47c is pressed against the valve seat 46b, whereby the flow channel is blocked and the flow toward the primary-side flow channel hole 9a is prevented.

Figure 9:
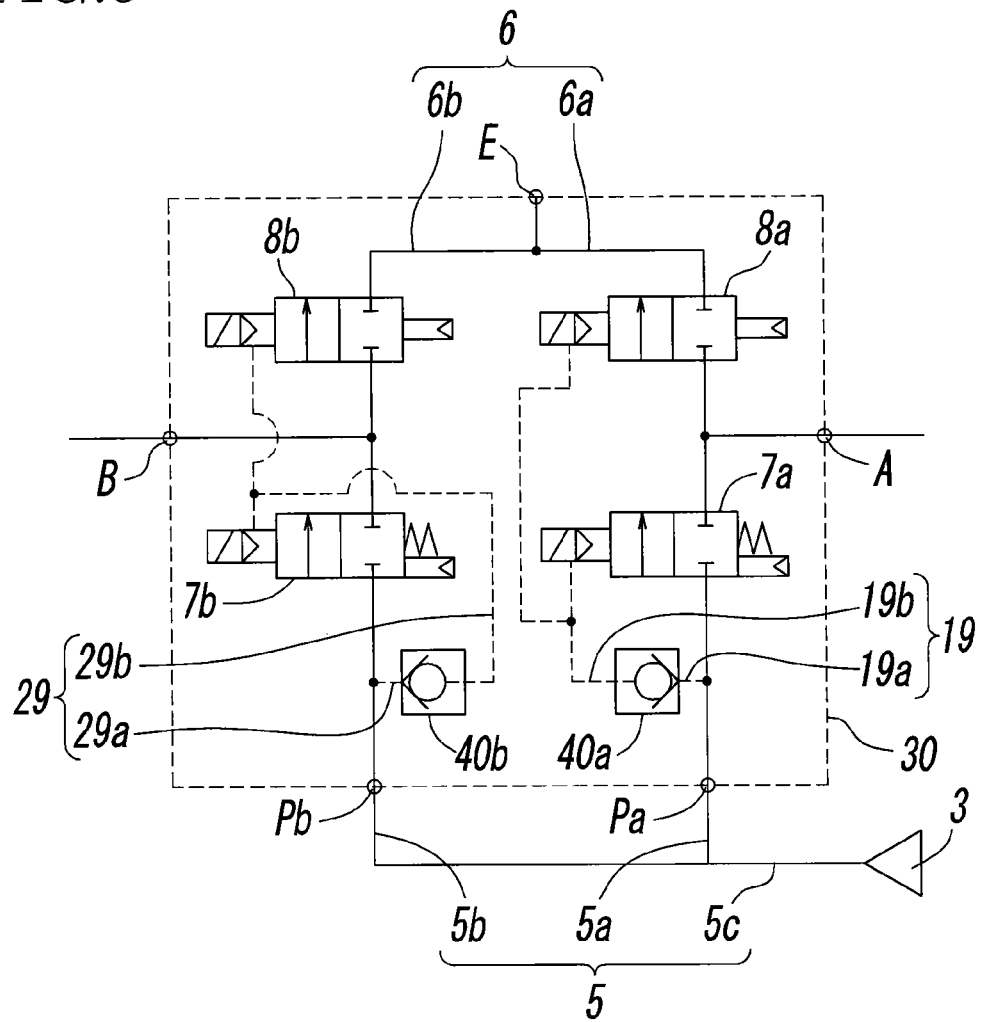
FIG. 9 is a schematic fluid circuit drawing of an oxygen generating portion illustrating another embodiment of an oxygen concentrator according to the present invention.
Figure 10:
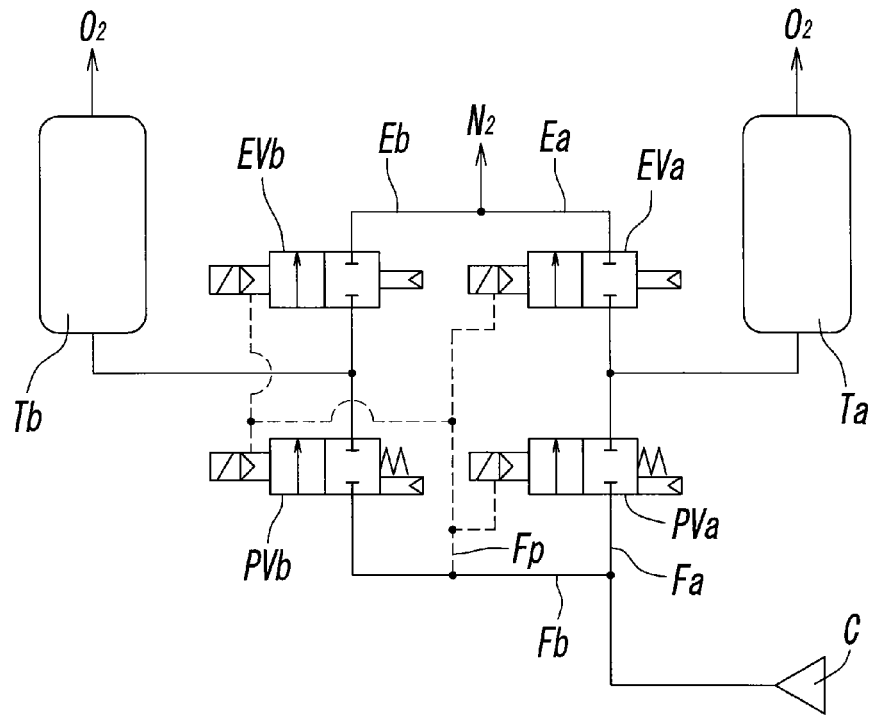
FIG. 10 is a schematic fluid circuit drawing illustrating a general oxygen concentrator.

FIG. 9 illustrates another embodiment of the oxygen concentrator 1 of the present invention. Here, in order to avoid overlapping of description, portions having different configurations from the oxygen concentrator 1 illustrated in FIG. 1 are mainly described, and description of the parts having the same configurations is omitted by denoting with the same reference numerals as those illustrated in FIG. 1.

In this embodiment, the main flow channel 5c of the air supply flow channel 5 is branched into the first branch flow channel 5a and the second branch flow channel 5b on the upstream side of the manifold base 30, and the manifold base 30 is provided with a first air supply port Pa and a second air supply port Pb for connecting the respective branch flow channels 5a, 5b.

A first pilot flow channel 19 configured to supply the pilot air to the electromagnetic pilot valves 20 of the first air supply valve 7a and the first exhaust valve 8a is branched from the first branch flow channel 5a in the manifold base 30, and a first pilot check valve 40a configured to prevent the pilot air from flowing reversely is provided at a position in the pilot flow channel 19 on the upstream side of the air supply valve 7a.

A second pilot flow channel 29 configured to supply the pilot air to the electromagnetic pilot valves 20 of the first air supply valve 7b and the second exhaust valve 8b is branched from the first branch flow channel 5b in the manifold base 30, and a second pilot check valve 40b configured to prevent the pilot air from flowing reversely is provided at a position in the pilot flow channel 29 on the upstream side of the first air supply valve 7a.

Specifically, in the manifold base 30, the first and second pilot flow channels 19, 29 include primary-side flow channel holes 19a, 29a on the upstream side and secondary-side flow channel holes 19b, 29b on the downstream side with the check valves 40a, 40b interposed therebetween, respectively, as those illustrated in FIG. 6 and FIG. 8, and these check valves 40a, 40b allow the pilot air to flow from the primary-side flow channel holes 19a, 29a to the secondary-side flow channel holes 19b, 29b and block the flow from the secondary-side flow channel holes 19b, 29b to the primary-side flow channel holes 19a, 29a.

Accordingly, as illustrated in FIG. 3, the pilot pressure is prevented from dropping in association with dropping of the air supply pressure immediately after having switched between the "first valve opening-and-closing pattern" and the "second valve opening-and-closing pattern", and the required pilot pressure can be maintained.

Although the embodiments of the oxygen concentrator of the present invention have been described thus far, the present invention is not limited to the above-described respective embodiments, and various modifications of design are possible without departing the gist of the present invention. For example, in the embodiment illustrated in FIG. 1, the pilot flow channel 9 is branched from the second branch flow channel 5b. However, the pilot flow channel 9 may be branched from the first branch flow channel 5a or, branched from the both branch flow channels 5a, 5b respectively in the same manner as the embodiment of FIG. 9. In addition, in the embodiment of FIG. 1, in the same manner as the embodiment of FIG. 9, the main flow channel 5c may be branched into the first and second branch flow channels 5a, 5b on the upstream side of the manifold base 30. In addition, in the embodiments illustrated in FIG. 1 and FIG. 9, the pilot flow channels 9, 19, 29 may be branched not from the branch flow channels 5a, 5b, but from the main flow channel 5c.

REFERENCE SIGNS LIST

1: oxygen concentrator
2: oxygen generating portion
3: compressor (compressed air supply source)
4A: first sieve bed
4B: second sieve bed
5: air supply flow channel
5a: first branch flow channel
5b: second branch flow channel
5c: main flow channel
6: exhaust flow channel
7a: first air supply valve
7b: second air supply valve
8a: first exhaust valve
8b: second exhaust valve
9. 19, 29: pilot flow channel
10: diaphragm valve
20: electromagnetic pilot valve
30: manifold base
40, 40A, 40a, 40b: pilot check valve (check valve)

The invention claimed is:

1. An oxygen concentrator comprising:
a compressed air supply source for outputting compressed air; first and second sieve beds including an absorbing material configured to selectively adsorb nitrogen from air under increased pressure and discharge the adsorbed nitrogen under reduced pressure integrated therein and configured to generate oxygen at a high concentration by separating nitrogen from the compressed air; an air supply flow channel supplying the compressed air from the compressed air supply source to the respective sieve beds respectively; an exhaust flow channel discharging exhaust air in each of the sieve beds to the atmosphere respectively, the air supply flow channel including a main flow channel connected to the compressed air supply source and first and second branch flow channels branched from the main flow channel and connected to the first and second sieve beds, first and second air supply valves provided respectively in the first and second branch flow channels and configured to communicate the compressed air supply source with the first and second sieve beds alternately; and an exhaust valve provided in the exhaust flow channel and configured to communicate the first sieve bed with the atmosphere when the first air supply valve is closed, and communicate the second sieve bed with the atmosphere when the second air supply valve is closed, wherein the air supply valves each include a diaphragm valve as a main valve and an electromagnetic pilot valve driving the main valve in a direction of closing the branch flow channel by pilot air, a pilot flow channel supplying the pilot air to the electromagnetic pilot valves is branched from a position on the upstream side of the air supply valves in the air supply flow channel, and a check valve preventing the pilot air from flowing reversely is provided in the pilot flow channel, wherein the first and second air supply valves and the exhaust valve are mounted on a single manifold base, the manifold base includes the air supply flow channel, the pilot flow channel branched from the air supply flow channel, the exhaust flow channel, and the check valve mounted therein, wherein the manifold base is provided with a check valve mounting hole for inserting and mounting the check valve from the outside formed therein, the pilot flow channel is formed by a primary-side flow channel hole extending from a side wall of the check valve mounting hole to the air supply flow channel and a secondary-side flow channel hole extending from an inner portion of the check valve mounting hole to the electromagnetic pilot valve, and wherein the check valve includes a hollow outer cylinder provided with a first opening configured to communicate with the secondary-side flow channel hole at an end in an axial direction, and is fitted in the check valve mounting hole with the first opening on the inner side, and a check valve main body configured to prevent pilot air from a hollow core cylinder disposed in the outer cylinder and the secondary-side flow channel hole from flowing reversely, the pilot air from the primary-side flow channel hole is introduced into the core cylinder through first and second air introducing holes formed on side walls of the outer cylinder and the core cylinder respectively, is derived out from the interior of the core cylinder through an air deriving hole provided on the core cylinder, and is guided to the first opening through the periphery of the check valve main body.

2. The oxygen concentrator according to claim 1, wherein one pilot flow channel supplying pilot air to both of the electromagnetic pilot valves of the first and second air supply valves is branched from the air supply flow channel.

3. The oxygen concentrator according to claim 1, wherein first and second pilot flow channels supplying pilot air to the respective electromagnetic pilot valves of the first and second air supply valves are branched respectively from the air supply flow channel.

4. The oxygen concentrator according to claim 1, wherein the check valve main body is an annular lip seal having a cross sectional shape of a V-shape opening on the first opening side of the outer cylinder.

5. The oxygen concentrator according to claim 2, wherein the check valve main body is an annular lip seal having a cross sectional shape of a V-shape opening on the first opening side of the outer cylinder.

6. The oxygen concentrator according to claim 3, wherein the check valve main body is an annular lip seal having a cross sectional shape of a V-shape opening on the first opening side of the outer cylinder.

7. The oxygen concentrator according to claim 1, wherein the air deriving hole is formed in an end surface of the core cylinder located at a position on the first opening side of the outer cylinder so that a poppet valve as the check valve main body provided in the outer cylinder comes into and out of contact with a valve seat formed so as to surround the air deriving hole.

8. The oxygen concentrator according to claim 2, wherein the air deriving hole is formed in an end surface of the core cylinder located at a position on the first opening side of the outer cylinder so that a poppet valve as the check valve main body provided in the outer cylinder comes into and out of contact with a valve seat formed so as to surround the air deriving hole.

9. The oxygen concentrator according to claim 3, wherein the air deriving hole is formed in an end surface of the core cylinder located at a position on the first opening side of the outer cylinder so that a poppet valve as the check valve main body provided in the outer cylinder comes into and out of contact with a valve seat formed so as to surround the air deriving hole.

10. The oxygen concentrator according to claim 1, wherein an air filter is mounted in the core cylinder so as to cover the second air introducing holes.

11. The oxygen concentrator according to claim 2, wherein an air filter is mounted in the core cylinder so as to cover the second air introducing holes.

12. The oxygen concentrator according to claim 3, wherein an air filter is mounted in the core cylinder so as to cover the second air introducing holes.

13. The oxygen concentrator according to claim 1, wherein a second opening is formed at the other end, which is on a side opposite to the first opening of the outer cylinder so that the core cylinder can be fit in the outer cylinder through the second opening, and the check valve mounting hole is hermetically closed by a sealing cap configured to close the second opening of the outer cylinder.

14. The oxygen concentrator according to claim 2, wherein a second opening is formed at the other end, which is on a side opposite to the first opening of the outer cylinder so that the core cylinder can be fit in the outer cylinder through the second opening, and the check valve mounting hole is hermetically closed by a sealing cap configured to close the second opening of the outer cylinder.

15. The oxygen concentrator according to claim 3, wherein a second opening is formed at the other end, which is on a side opposite to the first opening of the outer cylinder so that the core cylinder can be fit in the outer cylinder through the second opening, and the check valve mounting hole is hermetically closed by a sealing cap configured to close the second opening of the outer cylinder.

* * * * *